United States Patent
Cook

(10) Patent No.: US 11,850,231 B1
(45) Date of Patent: Dec. 26, 2023

(54) TRYTOPHAN METABOLIC STIMULATION COMPOSITIONS

(71) Applicant: Christina Rahm Cook, Brentwood, TN (US)

(72) Inventor: Christina Rahm Cook, Brentwood, TN (US)

( * ) Notice: Subject to any disclaimer, the term of this patent is extended or adjusted under 35 U.S.C. 154(b) by 15 days.

(21) Appl. No.: 17/500,070

(22) Filed: Oct. 13, 2021

(51) Int. Cl.
| | |
|---|---|
| A61K 31/4045 | (2006.01) |
| A61P 25/20 | (2006.01) |
| A23L 33/175 | (2016.01) |
| A23L 33/16 | (2016.01) |
| A23L 33/105 | (2016.01) |
| A23L 33/15 | (2016.01) |

(52) U.S. Cl.
CPC ........ *A61K 31/4045* (2013.01); *A23L 33/105* (2016.08); *A23L 33/15* (2016.08); *A23L 33/16* (2016.08); *A23L 33/175* (2016.08); *A61P 25/20* (2018.01); *A23V 2002/00* (2013.01)

(58) Field of Classification Search
CPC .................................................. A61K 31/4045
See application file for complete search history.

(56) References Cited

FOREIGN PATENT DOCUMENTS

WO WO-2012170883 A1 * 12/2012 ............... A23L 2/52

OTHER PUBLICATIONS

"What the Letters "USP" Mean on the Label of Your Medicine." (Dec. 17, 2015). Accessed Jun. 8, 2023. Available from: <https://qualitymatters.usp.org/what-letters-usp-mean-label-your-medicine>. (Year: 2015).*

Pranil, Thorung, et al. "Influence of pH, temperature, and light on the stability of melatonin in aqueous solutions and fruit juices." Heliyon. (2020), vol. 6, pp. 1-7 of 7. (Year: 2020).*

Cherasse, Yoan and Urade, Yoshihiro. "Dietary Zinc Acts as a Sleep Modulator." International J. of Molecular Sciences. (2017), vol. 18, pp. 1-12 of 12. (Year: 2017).*

* cited by examiner

*Primary Examiner* — John S Kenyon
(74) *Attorney, Agent, or Firm* — Gulf Coast Intellectual Property Group

(57) ABSTRACT

The present invention is a natural anthropogenic dietary supplement containing tryptophan in combination with vitamins as well as minerals in order to facilitate treatment of sleep disorders such as but not limited to jet lag disorder and circadian rhythm sleep disorder. The composition of the present invention facilitates increased metabolism of tryptophan. The compositions of the present invention are provided in either gel capsules or as a beverage dose for consumption. The compositions of the present invention include embodiments that incorporate as a part thereof calcium salts and magnesium salts. Vitamins such as but not limited to niacin are further included in embodiments of the composition of the present invention. Furthermore, additional natural ingredients further contribute to the makeup of the embodiments of the composition of the present invention.

4 Claims, 4 Drawing Sheets

TRYTOPHAN METABOLIC STIMULATION COMPOSITIONS

PRIORITY UNDER 35 U.S.C SECTION 119(E) & 37 C.F.R. SECTION 1.78

This nonprovisional application claims priority based upon the following prior United States Provisional Patent Application entitled: Natural Anthropogenic Microparticles Technology for Gel Pack and Beverages, Application No. 63/090,747 filed Oct. 13, 2020, in the name of Christina Cook, which is hereby incorporated by reference for all purposes.

FIELD OF THE INVENTION

The present invention relates generally to dietary supplements, more
specifically but not by way of limitation, a natural anthropogenic dietary supplement containing tryptophan in combination with vitamins such as but not limited to $B_3$, $B_6$ and $B_{12}$, as well as minerals to include but not limited to calcium and magnesium in order to facilitate treatment of sleep disorders such as but not limited to jet lag disorder and circadian rhythm sleep disorder.

BACKGROUND

Sleep patterns in individuals can be disrupted by many things such as but not limited to stress. The latency time to falling asleep, which is known as sleep onset latency is a measurable period of time. Oral dosing of L-tryptophan has been shown to alter mood in the direction of relaxation and a perception of reduced stress, owing to its incremental effects on serotonin synthesis in the central nervous system. Study data, including tryptophan depletion studies in humans has shown that tryptophan levels can be an important determinant of mood, cognition, and behavior ensuing transportation from plasma into the brain via the large amino acid transporters. Increased prevalence of air travel, especially across international time zones, has become a more normal occurrence for thousands of individuals. Many of these individuals travel for work and are expected to function well despite crossing multiple time zones as part of jet travel. Most if not all of these individuals suffer from jet lag disorder and they are often not working at peak performance. As such they can find themselves unfit for the tasks required of them because of the serious effects of circadian rhythm disturbance. Aside from sleep and stress problems, jet lag disorder can also cause fatigue, difficulty staying alert, gastrointestinal issues, anxiety and amnesia. Jet lag disorder arises as a consequence of circadian misalignment that occurs after crossing time zones too rapidly for the human circadian system to keep pace. The American Academy of Sleep Medicine defines jet lag disorder as a syndrome involving insomnia or excessive daytime sleepiness following travel across at least 2 time zones. It is a recognized circadian rhythm sleep disorder characterized by insomnia or excessive daytime sleepiness is associated with trans-meridian jet travel.

Tryptophan is an essential amino acid and it cannot be synthesized by the human body and as such must be part of our diet. Amino acids, including tryptophan, act as building blocks in protein biosynthesis and in addition, tryptophan functions as a biochemical precursor for serotonin (5-hydroxytryptamine; 5-HTP) and melatonin. After absorption, tryptophan is present in blood with twenty percent as the free amino acid and the remainder bound to plasma proteins. Tryptophan is transported into the central nervous system via the large neutral amino acids, where it is available for metabolism into 5-Hydroxytryptamine and eventually to melatonin. Tryptophan loading thereby indirectly improves sleep in adults with some sleep disturbance. Tryptophan metabolism to 5-Hydroxytryptamine provides positive effects in conditions where potentially depleted 5-Hydroxytryptamine levels exist. The metabolic pathway of tryptophan illustrates that L-tryptophan can metabolize to niacin, also known as vitamin $B_3$, initially involving the enzyme indoleamine 2,3-dihydrogenase via kynurenine. When niacin is co-dosed with tryptophan, metabolism is shunted in the direction of 5-hydroxytryptophan and on to 5-Hydroxytryptamine. Niacin dosing has the effect of sparing tryptophan, which can then be used to synthesize 5-Hydroxytryptamine. Tryptophan is known to be an essential amino acid that is critical in the natural production of both 5-Hydroxytryptamine and melatonin in humans. These neurotransmitters are seen as necessary for regular sleep as melatonin helps regulate the body's circadian rhythm, while 5-Hydroxytryptamine communicates a need for sleep to the brain. Melatonin is a hormone produced by the pineal gland, a small organ in the brain, which responds to light. Its production is stimulated by darkness and suppressed by light and it is understood to be a key to helping the mind to recognize when it is time to sleep and when to wake up. Vitamins and minerals that have been shown to drive L-tryptophan metabolism in the direction of 5-Hydroxytryptamine.

Accordingly, there is a need for a composition that combines particular vitamins and minerals with tryptophan so as to increase metabolism of the tryptophan in order to alleviate jet lag disorder and circadian rhythm sleep disorder.

SUMMARY OF THE INVENTION

It is the object of the present invention to provide a nutraceutical compositions having mixtures of two or more combinations of microscopic vitamin and mineral particles capable of being released in the gastrointestinal tract in combination with L-tryptophan and/or melatonin so as to stimulate metabolism thereof wherein the present invention is an admixture of L-tryptophan and melatonin and at least two natural anthropogenic microparticles indole dietary supplements including 5-hydroxytryptophan in combination with other substances such as but not limited to chamomile, hops, lemon balm, passionflower, valerian, kava, rosehips, GABA, green tea extracts, including L-theanine, L-threonine, L-carnitine, phenibut (β-Phenyl-γ-aminobutyric acid), zinc, vitamin A, vitamin C, vitamin D, ginko biloba, ginseng, lemongrass, Linden, passiflora, Hawthorne Berry, Milk Thistle, Root Extract, Rhodiola Rosea extract, St. John's Wort, Mucuna Pruriens.

Another object of the present invention is to provide various embodiments of a tryptophan metabolic stimulation composition for ingestion by a human wherein the preferred embodiment is provided in a gel capsule formulation or a beverage dose.

A further object of the present invention is to provide a nutraceutical compositions having mixtures of two or more combinations of microscopic vitamin and mineral particles capable of being released in the gastrointestinal tract in combination with L-tryptophan and/or melatonin so as to stimulate metabolism thereof wherein the composition will optionally contain calcium and magnesium salts.

Still another object of the present invention is to provide various embodiments of a tryptophan metabolic stimulation composition for ingestion by a human wherein the compositions of the present invention include natural anthropogenic microparticles indole dietary supplements such as tryptophan, 5-hydroxytryptophan and melatonin in combination with niacin.

An additional object of the present invention is to provide a nutraceutical compositions having mixtures of two or more combinations of microscopic vitamin and mineral particles capable of being released in the gastrointestinal tract in combination with L-tryptophan and/or melatonin so as to stimulate metabolism thereof wherein the compositions of the present invention include natural anthropogenic microparticles indole dietary supplements such as tryptophan, 5-hydroxytryptophan and melatonin in combination vitamin $B_6$.

Yet a further object of the present invention is to provide various embodiments of a tryptophan metabolic stimulation composition for ingestion by a human wherein the novel combinations of natural anthropogenic microparticles indole dietary supplements with calcium salts will assist in treatment of insomnia and other sleep-related problems.

Another object of the present invention is to provide a nutraceutical compositions having mixtures of two or more combinations of microscopic vitamin and mineral particles capable of being released in the gastrointestinal tract in combination with L-tryptophan and/or melatonin so as to stimulate metabolism thereof wherein the calcium salts include but are not limited to calcium chloride, calcium tartrate, calcium maleate, calcium lactate, calcium citrate, calcium phosphate, calcium acetate, calcium carbonate, calcium hydrogen carbonate, calcium lactate calcium fumarate, calcium sulfate, calcium bromide, calcium mesylate, calcium palmoate, calcium iodide, calcium nitrate, calcium gluconate and calcium methylsulfate.

Still an additional object of the present invention is to provide various embodiments of a tryptophan metabolic stimulation composition for ingestion by a human wherein the composition can include magnesium salts with acceptable magnesium salts including but not limited to magnesium chloride, magnesium tartrate, magnesium maleate, magnesium lactate magnesium citrate, magnesium phosphate, magnesium phosphate monobasic, magnesium phosphate dibasic, magnesium acetate, magnesium carbonate, magnesium lactate magnesium fumarate, magnesium stearate, magnesium sulfate, magnesium bromide, magnesium mesylate, magnesium disuccinate, magnesium palmoate, magnesium iodide, magnesium nitrate and magnesium methylsulfate.

Yet another object of the present invention is to provide a nutraceutical compositions having mixtures of two or more combinations of microscopic vitamin and mineral particles capable of being released in the gastrointestinal tract in combination with L-tryptophan and/or melatonin so as to stimulate metabolism thereof wherein the recommended dosing levels for the compositions of the present invention are based on a one hundred and fifty five pound individual.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
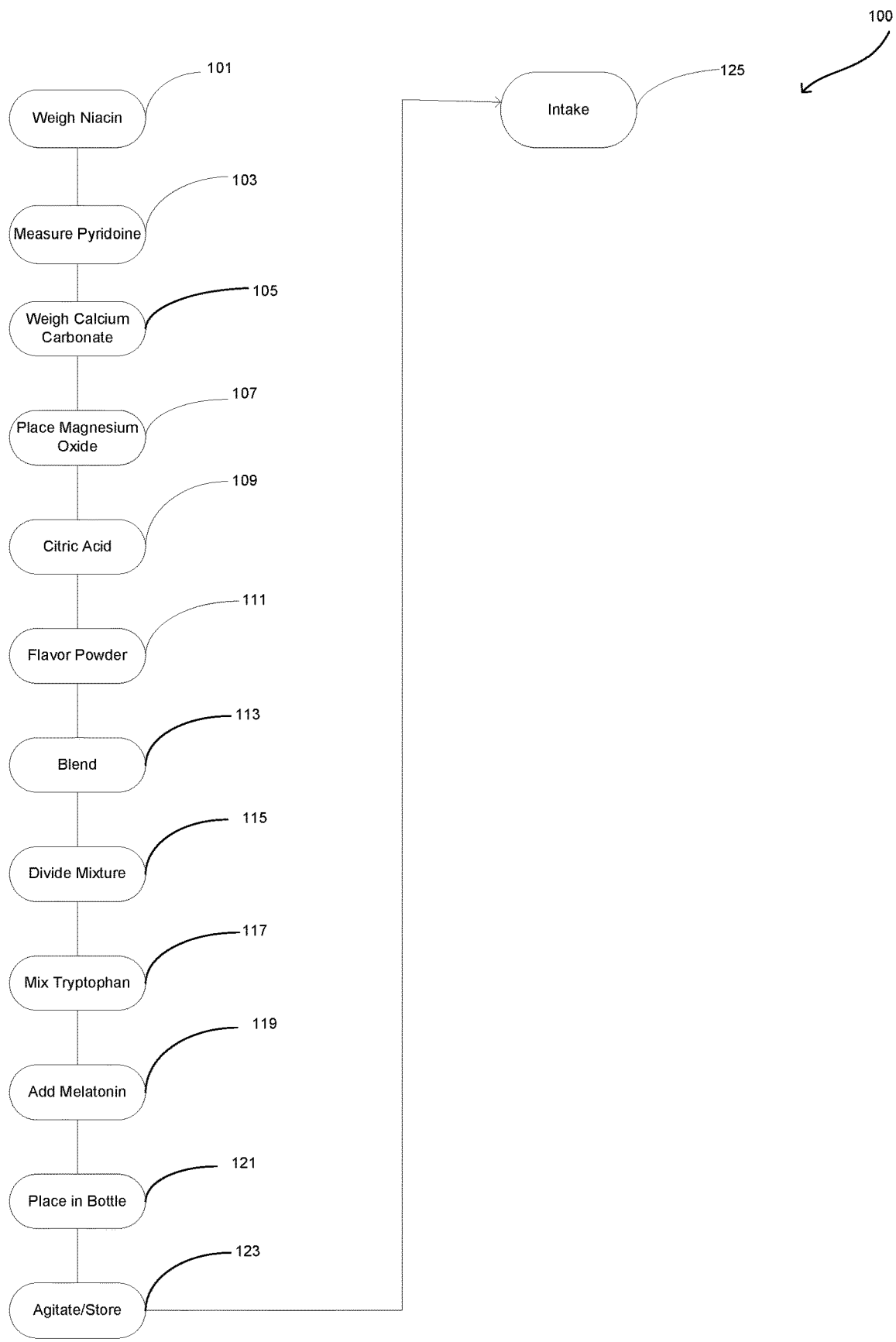
FIG. 1 is a method of producing an embodiment of the composition is outlined therein.

Referring now to the drawings submitted herewith, wherein various elements depicted therein are not necessarily drawn to scale and wherein through the views and figures like elements are referenced with identical reference numerals, there is illustrated a tryptophan metabolic stimulation composition 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted as a part hereof, the tryptophan metabolic stimulation composition 100 includes several preferred embodiments. Referring in particular to FIG. 1, step 101 an amount of Pyridine-3-carboxylic acid, also known as niacin is measured utilizing appropriate equipment. In a preferred embodiment of the present invention 0.010 grams of niacin is weighed and placed in a suitable container. It should be understood within the scope of the present invention that the amount of niacin and the other components listed herein could alter. By way of example but not limitation each of the components could vary in amount by approximately twenty percent. In step 103, 4,5-bis(hydroxymethyl)-2-methylpyridin-3-ol also known as pyridoxine is measured and placed in the container. In the preferred embodiment of the present invention 0.001 grams of pyridoxine is placed into the container. Step 105, a weight of two and a half grams of finely-powdered calcium carbonate is measured and placed into the container. In step 107, an amount magnesium oxide, specifically approximately three tenths of a gram was subsequently measured and placed into the container. Step 109 consists of approximately two grams of citric acid being measured and placed into the container. In step 111 a flavor powder was measured and placed into the container. In the preferred embodiment of the present invention the approximately five grams of the flavor powder is utilized. Additionally, it should be understood within the scope of the present invention that the flavor powder could be various different types of flavors such as but not limited to fruit flavor.

In step 113, the aforementioned components placed in the container are thoroughly mixed utilizing appropriate techniques. It should be understood within the scope of the present invention that agitation of the components in the container could be performed manually or with automated equipment. In step 115, the mixture disposed within the container is divided into ten equal parts by weight. The ten equal parts are placed in suitable individual containers. Step 117, the components stored in a single individual container is subsequently combined with USP grade (2S)-2-amino-3-(1H-indol-3-yl)propanoic acid, also known as L-tryptophan wherein the amount thereof is approximately six tenths of a gram. In step 119 the mixture has further added thereto N-[2-(5-methoxy-1H-indol-3-yl)ethyl]ethanamide also known as melatonin, wherein the amount of melatonin is approximately three one thousandths of a gram. Step 121, the final mixture is placed into one quarter of a liter bottle and an amount of two hundred and forty milliliters of water is subsequently added thereto. In step 123, the bottle is shaken/agitated utilizing appropriate techniques for at least two minutes and stored in a refrigerator at four degrees Celsius. In a preferred embodiment of the present invention the bottle is stored for at least six hours. Step 125, the resultant beverage embodiment of the present invention is available for consumption.

Figure 2:
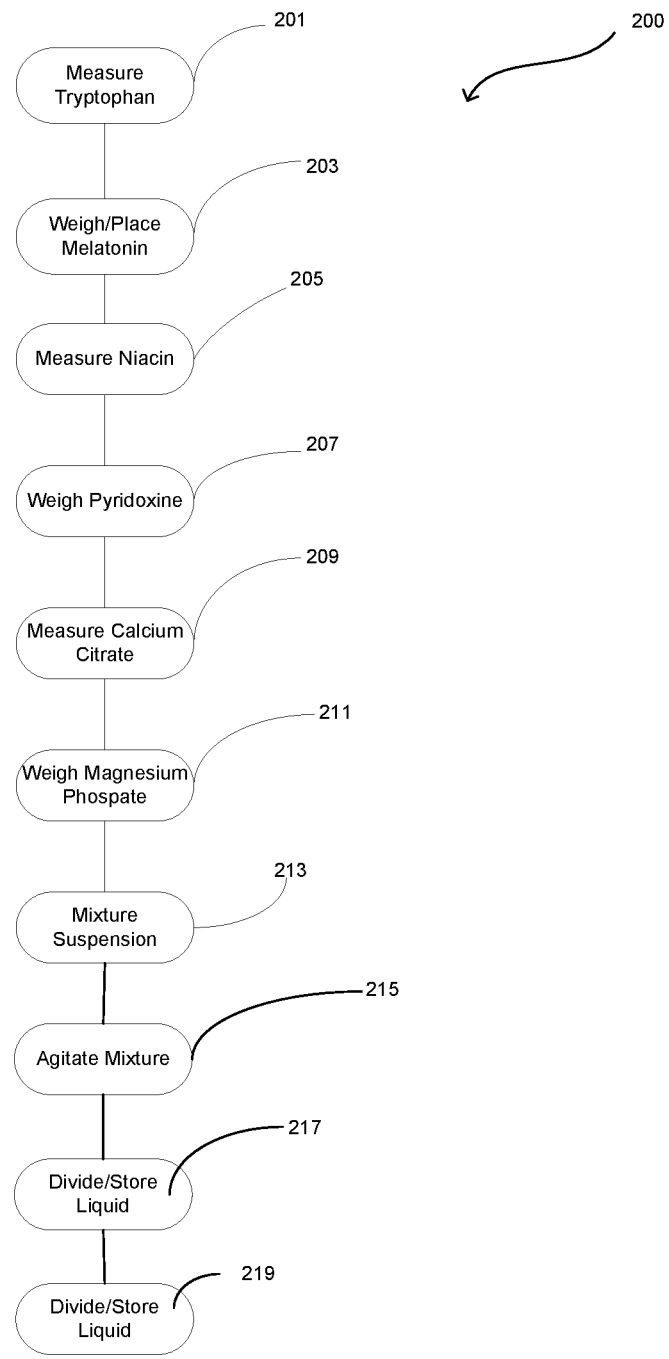
FIG. 2 is a method of producing an alternative embodiment of the composition is outlined therein.

Referring in particular to FIG. 2, an alternative embodiment of the tryptophan metabolic stimulation composition 200 is illustrated therein. In step 201 approximately three grams of USP grade (2S)-2-amino-3-(1H-indol-3-yl)propanoic acid, also known as L-tryptophan is measured and placed in an appropriate container. In a preferred embodiment of the present invention the container is a sterilized glass bottle Step 203 consists of weighing an amount of N-[2-(5-methoxy-1H-indol-3-yl)ethyl]ethanamide, also known as melatonin and placing in the container. In a preferred embodiment of the present invention approximately eight one hundredths of a gram of melatonin is utilized. In step 205, an amount of Pyridine-3-carboxylic acid also known as niacin is measured and placed into the container. In a preferred embodiment of the present invention approximately one tenth of a gram of niacin is measured and placed into the container. Step 207 approximately one-hundredth of a gram of 4,5-bis(hydroxymethyl)-2-methylpyridin-3-ol also known as pyridoxine is placed into the container. In step 209, approximately five grams of calcium citrate is measured and placed into the container. Step 211, approximately two grams of magnesium phosphate dibasic. In step 213 the aforementioned components of the tryptophan metabolic stimulation composition 200 are suspended in a pasteurized milk-based chocolate flavored gel pack or a liquid wherein the liquid consists of low-fat milk, sugar, cocoa processed with alkali corn starch, salt, carrageenan, vanillin, vitamin A palmitate and vitamin $D_3$. If suspended in a liquid the amount of the liquid is approximately one liter. Step 215, for either the gel pack or the liquid preparation the mixture is shaken utilizing a high-load orbital shaker for approximately one hour. In step 217, the liquid is dispensed in equal amounts into ten one hundred milliliter bottles and stored in a refrigerator at four degrees Celsius. In step 219 the tryptophan metabolic stimulation composition 200 is ready for consumption and subsequent testing of the effects of sleep patterns for the individual whom has consumed.

Figure 3:
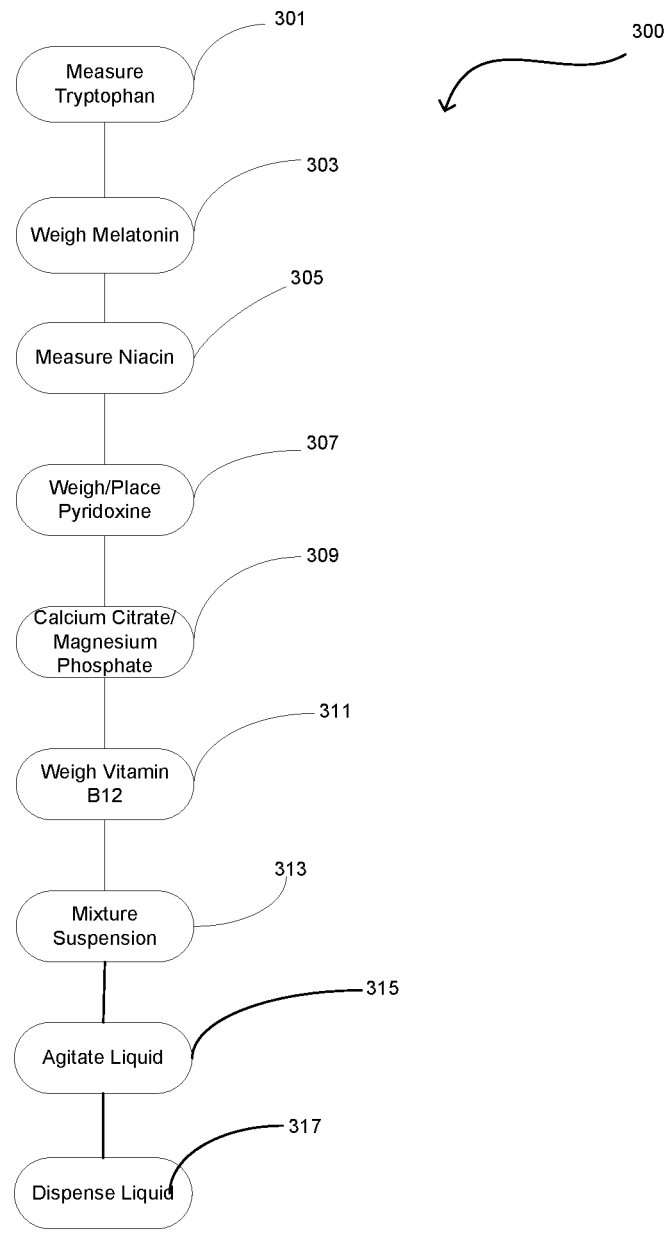
FIG. 3 is a method of producing an alternative embodiment of the composition is outlined therein.

Now referring in particular to FIG. 3, an alternate embodiment of the tryptophan metabolic stimulation composition 300 is diagrammed therein. In step 301, six grams of USP grade (2S)-2-amino-3-(1H-indol-3-yl)propanoic acid also known as L-tryptophan is measured and placed into a sterilized glass bottle. Step 303 an amount of N-[2-(5-methoxy-1H-indol-3-yl)ethyl]ethanamide also known as melatonin is measured and placed into the sterilized glass bottle. In a preferred embodiment of the tryptophan metabolic stimulation composition 300 approximately one-tenth to two tenths of a gram of melatonin is placed into the sterilized glass bottle. In step 305, approximately two-tenths of a gram of Pyridine-3-carboxylic acid also known as niacin is measured and placed into the sterilized glass bottle. Step 307, an amount of 4,5-bis(hydroxymethyl)-2-methylpyridin-3-ol also known as pyridoxine is measured and placed into the sterilized glass bottle. In a preferred embodiment two-hundredths of a gram of pyridoxine is placed into the sterilized glass bottle. In step 309, ten grams of calcium citrate and four grams of magnesium phosphate dibasic are measured and placed into the sterilized glass bottle. Step 311, one hundredth of a gram of vitamin $B_{12}$ is measured and placed in the sterilized glass bottle. In a preferred embodiment of tryptophan metabolic stimulation composition 300 the vitamin $B_{12}$ is used in a form known as cyanocobalamin, which converts to the active form in the body. In step 313, the aforementioned components of the tryptophan metabolic stimulation composition 300 are suspended in a pasteurized mango fruit drink wherein the mango fruit drink is a volume of two liters and comprises water, mango pulp sugar, citric acid and flavoring at room temperature. Step 315, the liquid is agitated utilizing a high-load orbital shaker for approximately one hour. Step 317, the resulting homogeneous sterile liquid suspension is dispensed in equal amounts into twenty one hundred milliliter containers and subsequently sealed and stored in a refrigerator prior to consumption by an individual.

Figure 4:
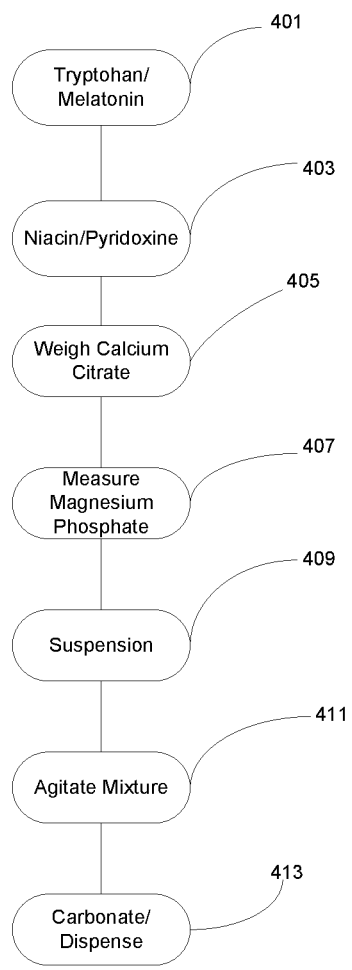
FIG. 4 is a method of producing an alternative embodiment of the composition is outlined therein.

Referring now to FIG. 4, an alternate embodiment of the tryptophan metabolic stimulation composition 400 is outlined therein. In step 401, three grams of USP grade (2S)-2-amino-3-(1H-indol-3-yl)propanoic acid also known as L-tryptophan and eight hundredths of a gram of N-[2-(5-methoxy-1H-indol-3-yl)ethyl]ethanamide also known as melatonin are weighed and placed into a sterilized glass bottle. Step 403 consists of measuring one tenth of a gram of Pyridine-3-carboxylic acid also known as niacin and one hundredth of a gram of 4,5-bis(hydroxymethyl)-2-methylpyridin-3-ol also known as pyridoxine and placing both into the sterilized glass bottle. In step 405 an amount of calcium citrate is added to the sterilized glass bottle. In the preferred embodiment of the tryptophan metabolic stimulation composition 400 approximately five grams of calcium citrate is weighed and placed into the sterilized glass bottle. Step 407 consists of weighing two grams of magnesium phosphate dibasic and placing into the sterilized glass bottle. In step 409, the aforementioned components of the tryptophan metabolic stimulation composition 400 are suspended in a pasteurized orange-based liquid wherein the liquid volume totals one liter. The liquid comprises water, orange juice and other desired flavoring and is mixed at room temperature. Step 411, the mixture is sealed and shaken utilizing a high-load orbital shaker for approximately one hour. In step 413, the sterile liquid is carbonated and dispensed in equal amounts into ten one hundred milliliter bottles wherein the bottles are sealed and stored in a refrigerator. It should be understood within the scope of the present invention that the tryptophan metabolic stimulation composition 400 could be embodied in a gel pack/capsule wherein the components thereof are suspended in suitable ingestible gel.

It is further contemplated within the scope of the present invention that a trace mineral complex could be included within the tryptophan metabolic stimulation composition 400 or any embodiment of the present invention herein. It is desired within the scope of the present invention that the trace mineral complex be present within an amount of approximately fifty milligrams. Additionally, microcrystalline cellulose in the amount of approximately one hundred and fifty milligrams could further be included. Furthermore, it is contemplated within the scope of the present invention that the tryptophan metabolic stimulation composition 400 or any embodiment thereof could further include Vitamin C at 1500 milligrams, Zinc Sulfate at forty milligrams and Vitamin D3 at 125 micrograms.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method for improving circadian rhythm sleep disorders in a human in an amount sufficient to treat symptoms associated with circadian rhythm sleep disorders wherein the method comprises the steps of:
    selecting an amount of melatonin, wherein the melatonin is provided in USP grade powder form;
    choosing calcium salt;
    mixing the calcium salt with the melatonin to create a mixture;
    suspending the mixture;
    dividing the mixture into ten equal portions by weight;
    placing the ten equal portions into individual containers;
    adding L-tryptophan to one of the individual containers, wherein the amount of l-tryptophan is six tenths of a gram;
    placing the mixture from one of said individual containers into a one quarter of a liter bottle:
    adding two hundred and forty milliliters of water to the one quarter of a liter bottle;
    storing the liquid in the one quarter of a liter bottle at four degrees centigrade for six hours; and
    administering the liquid to an individual.

2. The method for improving circadian rhythm sleep disorders as recited in claim 1, and further including a step of measuring and adding 0.010 grams of niacin to the mixture.

3. The method for improving circadian rhythm sleep disorders as recited in claim 1, and further including a step of measuring and adding five grams of calcium citrate to the mixture.

4. The method for improving circadian rhythm sleep disorders as recited in claim 1, and further including a step of measuring and adding an amount of two-hundredths of a gram pyridoxine to the mixture.

\* \* \* \* \*